United States Patent [19]

Volder

[11] 4,149,535

[45] Apr. 17, 1979

[54] CATHETER HOLDING DEVICE

[75] Inventor: Joy G. R. Volder, Rijswijk Netherlands

[73] Assignee: Gist-Brocades N.V., Delft, Netherlands

[21] Appl. No.: 794,411

[22] Filed: May 6, 1977

[30] Foreign Application Priority Data

May 6, 1976 [GB] United Kingdom ............... 18638/76
Aug. 20, 1976 [GB] United Kingdom ............... 34831/76

[51] Int. Cl.² ..................... A61M 05/00; A61M 25/00
[52] U.S. Cl. ................................ 128/214.4; 128/348; 128/DIG. 16
[58] Field of Search ............ 128/214.4, 221, 347–351, 128/DIG. 16, 262, 2 A, 2.05 D; 277/102, 108, 103

[56] References Cited

U.S. PATENT DOCUMENTS

| 3,589,356 | 6/1971 | Silverman | 128/262 X |
| 3,670,729 | 6/1972 | Bennett et al. | 128/214.4 |
| 3,970,089 | 7/1976 | Saice | 128/348 |
| 3,977,400 | 8/1976 | Moorehead | 128/214.4 |
| 4,037,600 | 7/1977 | Poncy et al. | 128/214.4 |

FOREIGN PATENT DOCUMENTS 804457 11/1958 United Kingdom ..................... 277/102

*Primary Examiner*—Dalton L. Truluck
*Attorney, Agent, or Firm*—Fleit & Jacobson

[57] ABSTRACT

A catheter holding device having longitudinally-extending walls defining an open-ended body with a main passage therethrough. At least a portion of the main passage is aligned with openings in forward and rear ends of the body. The portion of the walls adjacent the opening in the forward end of the body is adapted for receipt within a blood vessel or cavity. Another portion of the walls has a side opening allowing communication with the main passage. A side tube encompasses the side opening and extends from the body. Resilient material having a central passage therethrough is located within the side tube. The resilient material is designed to be compressed and grip a catheter which is passed through the material, into and through the main passage. A leading portion of the catheter projects beyond the forward end of the body. Clearance is left between at least one of the walls of the main passage and the catheter to allow simultaneous passage of liquids through both the main passage and the catheter. Thus, the catheter holding device is used for a number of dual functions, e.g., the simultaneous measurement of the central venous pressure and transfusion of liquids into the blood vessel.

15 Claims, 11 Drawing Figures

CATHETER HOLDING DEVICE

BACKGROUND OF THE INVENTION

This invention relates to an improved catheter holding device and more especially to such a device having a dual function.

FIELD OF THE INVENTION

Catheter holding devices to be punctured into a blood vessel are generally known, and are used, for example, to measure the central venous pressure (CVP) during serious operations in humans, e.g., heart operations, where it is highly desirable to follow the CVP. Such a puncture is normally applied in one arm of the patient or in a subclavian vein so that the CVP can be measured at a location as close as possible to the right heart auricle. If, during the operation, a fluid has to be given to the patient by transfusion, the other arm of the patient can be used for that purpose. However, if the CVP needs to be observed for an extended period of time, and if transfusions need to be given for longer periods of time, it may happen that an arm or puncture site of the patient comes into such a condition, e.g., because of inflammation of the arm, that it cannot be used any longer for catheterisation or transfusion. In that case, there is no arm or puncture site available to continue one of the functions. A prior art solution is the use of a catheter device as indicated in British Pat. Specification No. 1,284,537. That specification shows a device provided with a main bore for the passage of a catheter, and a side tube in connection with space around the catheter in the device, through which an anti-inflammatory liquid may be introduced, so that the area of the puncture will get inflamed much less easily. However, even if such a device is used, it is a disadvantage that both arms or puncture sites of the patient are occupied with devices punctured into blood vessels.

SUMMARY OF THE INVENTION

According to the present invention, there is provided a catheter holding device having longitudinally-extending walls defining an open-ended body with a main passage therethrough. At least a portion of the main passage is aligned with openings in forward and rear ends of the body. The portion of the walls adjacent the opening in the forward end of the body is adapted for receipt within a blood vessel or cavity. Another portion of the walls has a side opening allowing communication with the main passage. A side tube encompasses the side opening and extends from the body. Resilient material having a central passage therethrough is located within the side tube. The resilient material is designed to be compressed and grip a catheter which is passed through the material, into and through the main passage. A leading portion of the catheter projects beyond the forward end of the body. Clearance is left between at least one of the walls of the main passage and the catheter to allow simultaneous passage of liquids through both the main passage and the catheter. Suitably, the means for compressing the resilient material comprises a plug insertable into an open end of the side tube and having a bore or passage therethrough for the passage of the catheter into the side tube. Means are provided for securing the plug in a position compressing the resilient material and conveniently these means are capable of securing the plug in two alternative positions. In one position, the resilient material is compressed and in the other, it is relaxed to permit ready sliding of the catheter through the passage. Suitably, the securing means comprises a bayonet type connection between the plug and the side tube. Alternatively, the resilient material forms part of a cap adapted to be attached to the side tube of the catheter device, the cap having a central bore or passage defined by an inner resilient wall. In one embodiment, a resilient tube also defines the passage. The inner cross-section of the bore and/or tube are such that a catheter may slidingly pass therethrough. If such a cap is provided with a resilient tube, a liquid pressure, e.g., blood pressure, will act on the resilient tube so as to urge it tightly to fit around the catheter therethrough.

Preferably the resilient material, under pressure, is closed up in the side tube, closed by a plug fixed onto the side tube end, the resilient material and the plug leaving open a passage or canal through which the catheter may sealingly be passed. This embodiment is easier to be manufactured than both above-indicated embodiments, while the catheter device is easier to be handled in practice.

In another embodiment, the side tube is constricted between the resilient material and the point where it is connected with the main passage. Constriction is by means of an aperture plate extending across the side tube, by means of a simple reduction in diameter of the side tube, or by the size of the opening in the side wall of the main passage. With this latter arrangement, the side wall of the main passage has an aperture therethrough surrounded by a flange projecting into the side tube for convenient guiding of the catheter from the passage through the resilient material into the main passage. In order to improve connection between the forward end of the main passage and the interior of a blood vessel in which it is received, a plurality of openings, such as slits or holes, is provided through the walls of the forward end portion of the body.

Suitably the main passage has a wider diameter rear end portion to which the side tube is connected and a narrower diameter forward end portion adapted for receipt within a blood vessel. The body is adapted in its rear end for connection to an intraveneous system. Conveniently, a needle is provided for receipt within the main passage to project from the forward end thereof for puncturing a blood vessel for receipt of the forward end of the device.

Alternatively, the connection of the side tube and the main body are of a flat triangular construction, in which the side tube is formed in one of the edges of the triangularly shaped body. This construction is advantageous for mass production.

In its preferred forms, as later described in detail, the catheter holding device is used for a number of different functions. Primarily it permits both the measurement of the CVP and the transfusion of liquids into the blood vessel through a single puncture site with both functions being carried out simultaneously. In general, the preferred device is used for a number of purposes, for example, long term intravenous nourishment in combination with the possibility of simultaneous admission of other fluids or medicine, simultaneous administration of blood and fluids by a single puncture, monitoring of CVP in combination with the possibility of measuring venous blood gas values without interrupting the CVP measuring procedure, monitoring arterial blood pressure and arterial blood gas values by using a device through a single arterial puncture, and using a single puncture for permitting dialysis (hemodialysis) with blood being simultaneously passed through the device both into and out of the blood vessel, or permitting oxygenation of blood with patients having, e.g., an inferior lung function. In a greater design, the catheter device according to the invention is suitable for peritoneal dialysis.

In order to utilize the catheter holding device, a needle is first inserted into the main passage so as to project beyond the forwardmost end of the body of the device. The needle is used to puncture a blood vessel or body cavity and the forwardmost end of the body of the device is slid into the blood vessel or cavity with the needle being retracted. The rearward end of the body of the catheter device is then connected to an intravenous system, for example, a system for the transfusion or sampling of blood. After this connection has been made, a catheter is slid through the side tube into the main passage and out through the forward end of the main passage and into the blood vessel to the extent required for the function to be carried out. Thus, a CVP can be transmitted through the catheter and be observed therefrom by conventional means. Liquid introduced through the intraveneous system must flow through the forward end of the main passage around the catheter to reach the blood vessel and it is for that reason that it is preferred to provide the forward end of the main passage with a number of openings in order to decrease the pressure necessary to introduce the transfusion liquid into the blood vessel. As will be appreciated, once the catheter has been advanced to the required extent it is gripped in the device and sealed in location simply by causing compression of the resilient material by the plug.

The body of the resilient material in the side tube of the catheter is made from any suitable material, for example, expanded porous polytetrafluoroethylene, hydrophobic foamed rubber, silicon rubber and any other so-called bio-material that is resiliently compressible and conveniently sterilized.

As previously indicated, the catheter holding device is used in connection with dialysis apparatus to achieve a single needle dialysis connection. Blood is intercepted from a shunt in which the catheter holding device is inserted to extend in either an upstream or downstream direction. If it is inserted in an upstream direction, the blood is intercepted by the catheter and passes therethrough to the dialysis apparatus from which it is returned to the blood vessel by a passage through the main passage of the catheter holding device. If the device is inserted in a downstream direction, the blood in the blood vessel is intercepted to pass through the main passage of the catheter holding device around the catheter and is returned to the blood vessel through the catheter. Where the catheter holding device is intended for use primarily for dialysis purposes, the forward end of the main passage for insertion into the blood vessel will normally be both shorter and of wider diameter than where the catheter holding device is intended for use simultaneously to transfuse liquids into the blood vessel and to take a CVP.

While the catheter holding device is designed primarily for use in human surgery it is, of course, also suitable for use in experimental work.

BRIEF DESCRIPTION OF THE DRAWINGS

The invention will be further described, by way of example, with reference to the accompanying drawings; wherein.

DETAILED DESCRIPTION OF THE PREFERRED EMBODIMENTS

Figure 1:
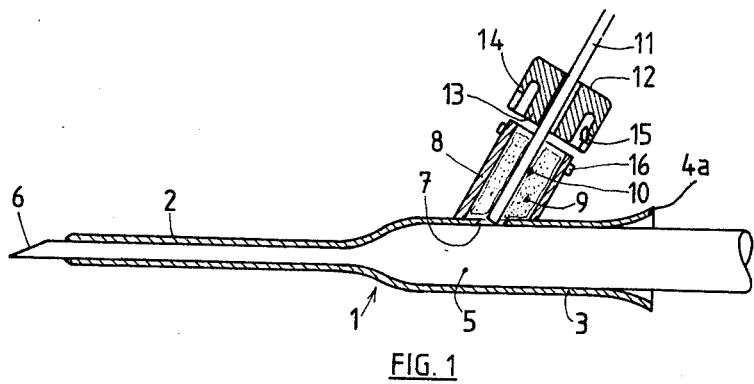
FIG. 1 is a longitudinal sectional view through a catheter holding device according to the invention in condition ready for puncturing and insertion into a blood vessel.

Referring to the drawings, FIG. 1 shows a first embodiment of a catheter holding device comprising longitudinally extending walls defining a body 1 having a smaller diameter forward end portion 2 and a larger diameter rearward end portion 3. Shown in FIG. 1 is a needle 5 received within a main passage extending lengthwise through the body 1, a forward end 6 of the needle projecting from the forwardmost end portion 2 of the body. At least a portion of the main passage is aligned with openings in the forward and rear ends of the body. As shown, needle 5 in its operative position is closely received within the main passage through the body. A side tube 8 projects laterally from the rearward portion of the body and encompasses an opening or aperture 7 in a wall of the body. The aperture 7 allows communication between the main passage 4 and the side tube 8 and is of sufficiently large diameter for the passage therethrough of a catheter 11. The side tube 8 is either attached to or formed as an integral part of the body 1. Within the side tube 8 there is received resilient material 9, by way of example in the form of a porous expanded polytetrafluoroethylene, the resilient material having a passage 10 therethrough aligned with the aperture 7 for the receipt of the catheter 11. A closure plug is provided for compressing the resilient material 9 within the side tube, the closure plug being in the form of a plug 13 and a cap 12 having an outer flange 14. A bayonet pin 16 and slot 15 connection in provided whereby the cap 12 can be secured on the side tube 8 with the plug 13 received therein compressing the resilient material 9 so that the resilient material grippingly sealingly engages the catheter 11 due to the consequent reduction in the cross-section of the passage 10.

Figure 2:
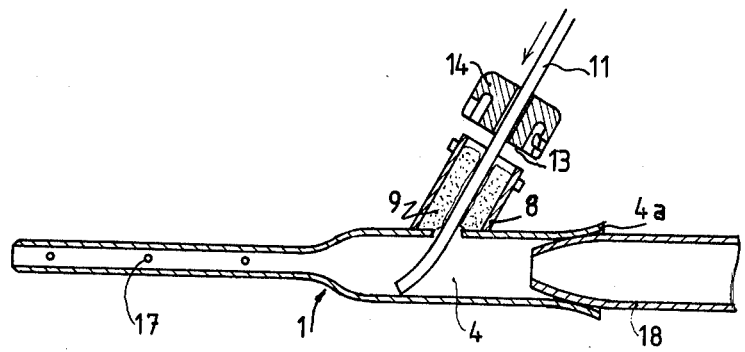
FIG. 2 is a view similar to FIG. 1, but in which the puncturing needle has been removed and has been replaced by a connection to an intravenous liquid supply system and in which a catheter projects into a main passage through the catheter holding device.

FIG. 2 shows the catheter 11 partly inserted into the main passage 4 of the body 1 and also shows the provision of openings, such as slits or holes 17, through the walls of the forward narrower diameter portion of the main passage. The rearward end of the main passage is flared at 4a to receive connection 18 from an intravenous system, such as a system for the transfusion of blood as shown in 10. It will be appreciated that other means well known to those skilled in the art can be used for connecting an intravenous system to the main passage 4 of the catheter holding device, for example, by clipping the system to the rear end of the catheter holding device by means of LUER LOCK.

Figure 3:
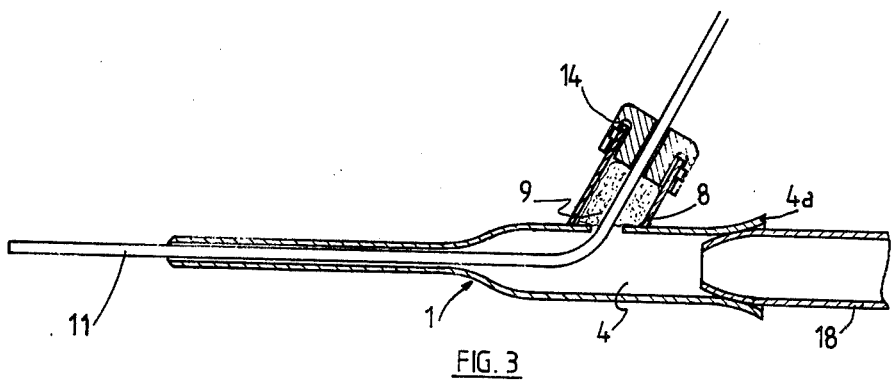
FIG. 3 is a view similar to FIG. 2, in which the catheter has been pushed through the catheter holding device to project from the forward end thereof.

FIG. 3 shows the device in its operating condition with the catheter 11 having been pushed sufficiently far into the main passage 4 for it to extend beyond the forward end thereof and with the plug 13 secured in position compressing the resilient material 9 so that the resilient material sealingly grips the catheter.

The catheter holding device of FIGS. 1 to 3 is used by taking the device in the configuration as shown in FIG. 1, with the needle 5 projecting from the forward end of the main passage 4, and is introduced into a blood vessel, for example a vein, shunt or an artery. Once it has been introduced into the vessel to the depth required, the needle 5 is retracted and an intravenous system is connected to the rear end of the device as shown in FIG. 2. The catheter 11 is then pushed into the main passage 4 until it projects as far as required beyond the forward end of the main passage into the blood vessel. Once the catheter 11 has been introduced sufficiently far into the blood vessel, the plug 13 is pushed home and secured by the bayonet connection 15 and 16 so as to compress resilient material 11 so that resilient material 11 is forced into tight engagement with the inside surface of the tube 8, the outer wall of the body 1 within the confines of the tube 8 and the periphery of the catheter 11 where it passes through the passage in the resilient material. This pressing engagement of the resilient material is sufficient to provide an adequate seal to avoid liquid leaking through the side tube 8 from the inside of the catheter holding device. Liquid introduced from the intravenous system flows into the main passage 4, flows around the catheter 11 into the smaller diameter portion of the main passage 4 and out through the holes 17 and the forward opening the main passage 4 to the blood vessel.

Figure 4:
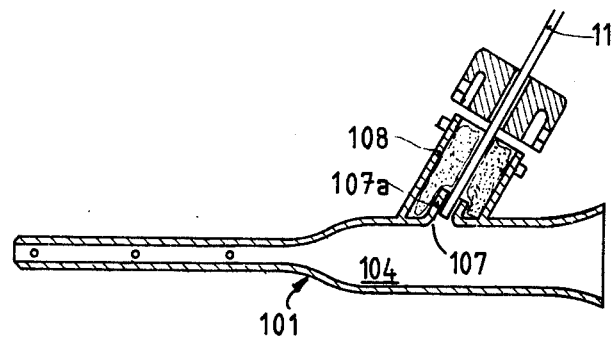
FIG. 4 is a longitudinal sectional view through a catheter holding device similar to that of FIGS. 1 to 3, but in which a modified aperture is provided for the passage of the catheter into the main passage of the device.

The embodiment of FIG. 4 is similar to that of FIGS. 1 to 3 and similar components have been identified by numbers above 100, i.e., side tube 8 in FIGS. 1-3 is identified as 108. In FIG. 4, a flange 107a is provided around the aperture 107 projecting into the side tube 108. The flange 107a provides a short tube permitting good centering of the catheter 11 so that the catheter can be supported at its forward end by the body 101 when retracted from the main passage 104 to ensure that it can readily be slid into the main passage without being caught up once the needle 5 has been withdrawn from the main passage 104.

Figure 5:
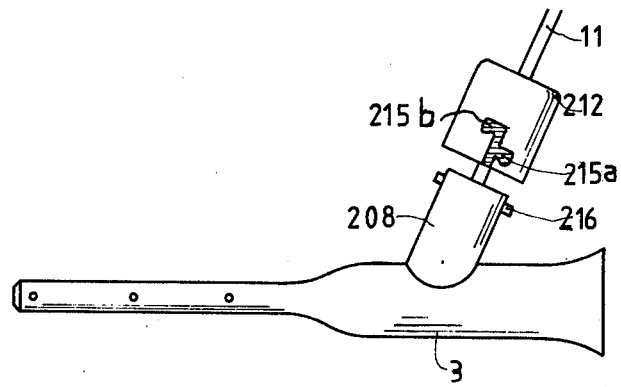
FIG. 5 is a side view of an embodiment similar to that of FIGS. 1 to 3, but having a modified closure plug for a side tube through which the catheter is insertable into the main passage of the device.

FIG. 5 illustrates a modification of the closure plug of FIGS. 1-4. Similarly components have been identified by numbers above 200. The closure plug of FIG. 5 uses a bayonet device with two alternative slots, 215a and 215b, for retaining the cap 212 over the end of the side tube 208. When the pin 216 is engaged in bayonet slot 215a, the cap 212 is retained over the end of the side tube 208 without substantially any compression of the resilient material. When the cap 212 is pushed home to engage slot 215b, the plug 213 compresses the resilient material as described above. This construction assists the alignment of the catheter 11 when it is being pushed into the catheter holding device and into the blood vessel because of the plug remaining in a secured position at that time with a consequent sufficient guiding of the catheter as it passes through the bore in the plug portion of the cap 212.

Figure 6:
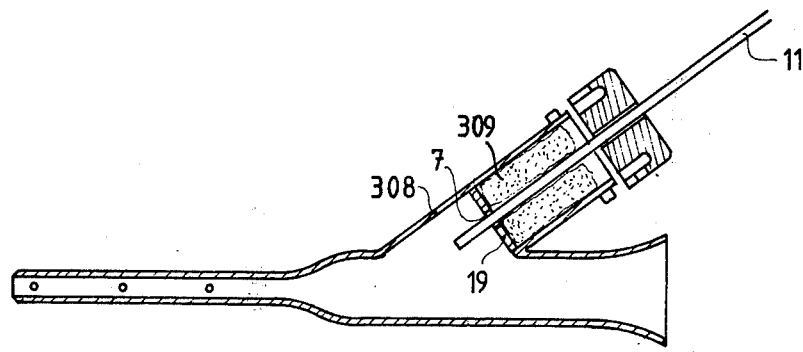
FIG. 6 is a view similar to that of FIG. 4 but showing a further modified embodiment.

In the embodiment of FIG. 6, numbers above 300 have been used to identify components similar to those described in FIGS. 1-5. In FIG. 6, a constriction is provided at the lower end of the side tube 308. The constriction is obtained by any one or combination of the following: an aperture plate 19 received in side tube 308, as shown in FIG. 6; a reduction in the size of aperture 7, as shown in FIGS. 1-3; and a reduction in the diameter of the side tube, as at 22 in FIG. 7. With the constriction, the resilient material 309 is a simple annular block which is easily replaced and located in position in the tube 308 without any difficulties of alignment. This general arrangement assists the insertion of the catheter 11 in a sterile state.

Figure 7:
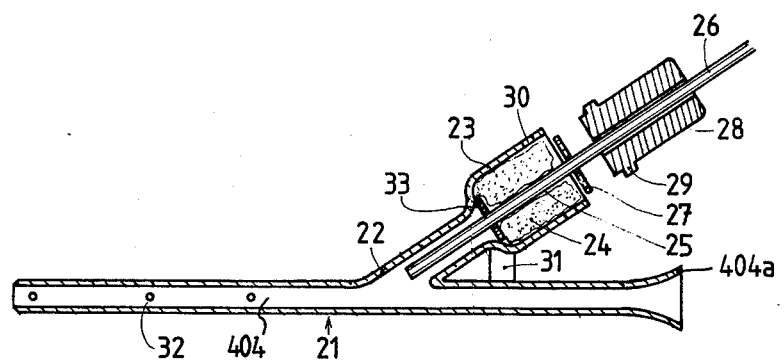
FIG. 7 is a view similar to FIG. 4 but showing yet another embodiment of the catheter holding device.

FIG. 7 illustrates yet another embodiment of the invention in which numbers above 400 have been used to identify components similar to those previously described. In FIG. 7, a main body 21 has substantially the same cross-section over its entire length except for a flared entry 404a for connection with an intravenous system. Holes 32 similar to the holes 17 are provided through the walls of the main passage 404 in the forward end of the device with the side tube 22 having an enlarged end part 23. A resilient annular block or body 24 of porous expanded polytetrafluoroethylene has a central passage 25 for the catheter 26. A ring 27 is provided about the catheter 26 between the porous material 24 and a plug 28 adapted to be secured in position compressing the block 24 by means of a bayonet pin and stop connection 29 and 30. A reinforcing member 31 is shown provided between the portion of the body 21 and the side tube for rigidifying the structure and, in general, this arrangement operates in a similar manner to the device of FIGS. 1 to 3 in that the plug 28 is pushed into the open end of the side tube 22, 23 so as to cause the ring 27 to compress the resilient material block 24. While the constriction provided by the reduction in diameter of the side tube passing from the portion 23 to the portion 22 is usually adequate to retain the resilient material for compression, a further ring 33 is provided at the narrow end as a second restriction to ensure proper compression of the resilient material. The bayonet connection is provided with a two position locking arrangement for securing the plug into two possible axial positions for operation in the same manner as described above in connection with FIG. 5.

The catheter device 1, 101, 21 is made of either opaque material, for example, stainless steel or plastics, or, preferably, a transparent material, for example, a styrene polymer or copolymer, so that what is occurring within the catheter device during use thereof can be seen from the outside.

Figure 8:
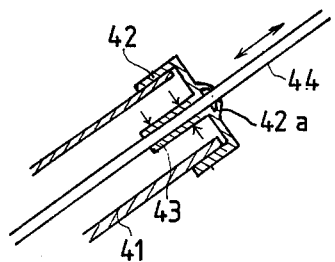
FIG. 8 is a section through a detail of another embodiment showing a cap with a resilient part, through which a catheter passes.

FIG. 8 shows an embodiment in which the body of resilient material forms part of a cap 42 closing a side tube 41, with a catheter 44 being passed through the cap. Side tube 41 is provided with the cap closing tightly the side tube. The cap 42 is provided with a central passage or bore in connection with a small tube 43 at the inner side of the cap, through which tube the catheter 44 slidingly passes. When the catheter device of this type is in use, the inner space of the side tube will be filled with liquid, e.g., blood, which will exert sufficient pressure on the outside of the small tube 43 to cause it to fit tightly around the catheter, and leakage is avoided to a high extent. The cap is preferably made of a suitable resilient material such as rubber of a resilient plastics material. In order to keep the catheter in its desired position relative to the cap, protrusions 42a are provided near the central bore of the cap for gripping the catheter.

Figure 9:
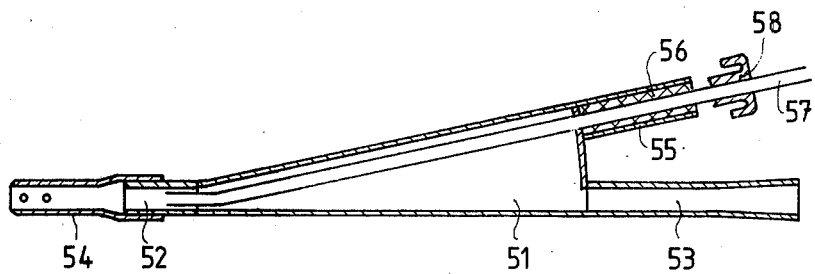
FIG. 9 is a view similar to FIG. 4, but in which the main body is of a special shape.

FIG. 9 shows an embodiment in which the connection of the side tube to the main body is formed by a triangularly shaped housing. A triangularly shaped, box-like housing 51 is provided with tubes 52 and 53 which are in line, so that a needle may be passed therethrough. The foremost tube 52 is provided with a medical device, such as a canula 54, attached to the foremost end of the tube 52. The end of the medical device fits tightly around or just inside the end of the tube 52. The tubes 52 and 53, together with canula 54, are aligned to allow passage by a needle for puncture into a blood vessel.

The rear edge of the triangular housing 51 is provided with another tube 55 with a resilient body 56 passed by a catheter 57 and closable with a cap 58 as explained hereinbefore. The embodiment shown in FIG. 9 is adapted to be manufactured in mass production. Further, the construction facilitates removal of undesired air bubbles from the catheter device.

Figure 10:
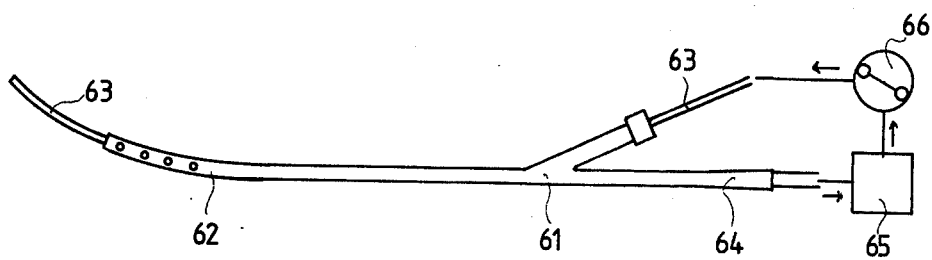
FIG. 10 is a side view of still another embodiment which is especially suited for use in oxygenation of blood with patients having an inferior lung function.

FIG. 10 illustrates an embodiment especially adapted to oxygenating blood with patients having an inferior lung function (e.g., pre- or postoperative). The catheter device 61 shown in this Figure is provided with a shaped flexible foremost tube 62, as shown in FIG. 10. The tube 62 used with this embodiment, is inserted via the greater staphenus vein into the femoral vein, or directly in the femoral vein, and a catheter 63 is pushed so far as to end near the heart. The rear end of the main tube 64 is connected to an oxygenator 65, also called an auxiliary lung, which in turn is connected to a pump 66, e.g., a roller peristaltic or other pulsating pump, and back to the catheter 63. The oxygenator and the pump are interchangeable in relation to the catheter and the main tube 64.

Figure 11:
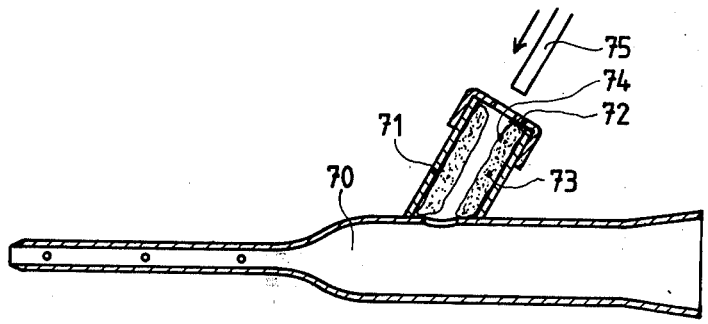
FIG. 11 is a longitudinal sectional view through another embodiment of the catheter holding device according to the invention, in which the plug is fixed onto the side tube.

FIG. 11 shows an embodiment of the catheter holding device according to the invention, in which the plug is fixed onto the side tube. The main tube 70 of the catheter holding device is provided with a side tube 71, closed by a fixed plug or cap 72. The space within the side tube 71 is filled up with a resilient material, under pressure, leaving open a central passage or canal 74 in the middle of it, in line with a central opening in the cap 72. A catheter 75 is passed through the central opening which avoids liquid leaking from the inside of the catheter device to the outside by sealing closure of the catheter against the wall of the canal by the resilient material under pressure.

While embodiments of the apparatus according to the invention have been illustrated and described herein in considerable detail, the invention is not to be considered limited to the embodiments. Other adaptations, modifications and uses of the invention may occur to those skilled in the art to which the invention relates, and it is intended to cover all such adaptations, modifications and uses which come within the scope of the appended claims.

What is claimed is:

1. A catheter and catheter holding assembly comprising: longitudinally-extending walls defining an open-sided body having a main passage therethrough, at least a portion of said main passage being aligned with openings in forward and rear ends of said body, the portion of said walls adjacent openings in the forward end of the body being adapted for receipt within a blood vessel or cavity, a second portion of said walls having a side opening therethrough allowing communication with said main passage, and the portion of said walls adjacent the opening in the rear end of the body being adapted for connection to an intravenous system; a side tube extending from said body having one end encompassing said side opening and the other end being open; resilient material received within the side tube, said resilient material having a passage therethrough, said a catheter being removably passed therethrough into the main passage for projection from the forward end thereof with clearance being left between at least one of the walls of the main passage and the catheter so that fluid communication paths through the catheter and through the main passage external of the catheter can be simultaneously established; and means for compressing the resilient material in the side tube to reduce the cross-section of the passage through the resilient material for sealingly gripping said catheter passing therethrough.

2. A catheter assembly as claimed in claim 1, wherein the means for compressing the resilient material comprises a plug inserted into the open end of the side tube, the plug having a passage therethrough for the passage of the catheter into the side tube.

3. A catheter holding device as claimed in claim 2, wherein the resilient material is compressed in the side tube by the insertion and attachment of the plug to the open end of the side tube, the resilient material and the plug leaving open a passage through which the catheter may sealingly be passed.

4. A catheter holding device as claimed in claim 2, wherein said means for compressing further comprises means for securing the plug to the side tube in a position compressing the resilient material.

5. A catheter holding device as claimed in claim 4, wherein the means for securing the plug comprises means for securing the plug in a first position in which the resilient material is compressed and means for securing the plug in a second position in which the resilient material is substantially uncompressed to permit ready sliding of the catheter through the passage.

6. A catheter holding device as claimed in claim 5, wherein the securing means comprises a bayonet type connection between the plug and the side tube.

7. A catheter holding device as claimed in claim 1, wherein the side tube further includes a cap mounting onto the open end of the side tube of the catheter device, said cap having a central passage defined by an inner resilient wall, the inner cross-section of at least one of said passages in said cap and said resilient material being sufficiently large that a catheter may slidingly pass therethrough.

8. A catheter holding device as claimed in claim 1, further comprising means for constricting the side tube between the resilient material and the point where the side tube extends from the housing.

9. A catheter holding device as claimed in claim 8, wherein said means for constricting comprises an apertured plate extending across the inside to the side tube.

10. A catheter holding device as claimed in claim 9, wherein the side opening in the body is surrounded by a flange projecting into the side tube for convenient guiding of the catheter from the passage through the resilient material into the main passage.

11. A catheter assembly as claimed in claim 8, wherein said means for constricting comprises said side tube having a diameter between the resilient material and the point where the side tube extends from the housing that is reduced from the side tube diameter that supports the resilient material.

12. A catheter assembly as claimed in claim 8, wherein said means for constricting comprises a portion of the wall encompassing the side opening.

13. A catheter holding device as claimed in claim 1, wherein a plurality of openings are provided through said portion of said walls adjacent the opening in the forward end of the body.

14. A catheter assembly as claimed in claim 1, wherein the main passage has a wider diameter in the vicinity of said side opening and a narrower diameter in the portion of said walls adapted for receipt within a blood vessel.

15. A catheter and catheter holding assembly comprising:

a hollow triangular shaped body having the vertexes thereof open, the opening in one of said vertexes being connected to a device adapted for receipt within a blood vessel or cavity, the opening in a second or said vertexes being connected to a side tube, the opening in a third of said vertexes being adapted for connection to an intravenous system; resilient material received within the side tube, said resilient material having a passage therethrough, said a catheter being removably passed therethrough into and through said body for projection from the forward end of the device connected to said opening in said one vertex with clearance being left between at least one of the sides of the connected device and the catheter so that fluid communication paths through the catheter and through the connected device external of the catheter can be simultaneously established; and means for compressing the resilient material in the side tube to reduce the cross-section of the passage through the resilient material for sealingly gripping said catheter passing therethrough.

* * * * *